(12) United States Patent
Dawood et al.

(10) Patent No.: US 6,547,565 B1
(45) Date of Patent: Apr. 15, 2003

(54) ARRANGEMENT FOR AN INSTRUMENT WHICH COMPRISES OR IS CONNECTED TO A DRIVING-IN TOOL

(75) Inventors: Andrew Dawood, London (GB); Anders Petersson, Gothenburg (SE)

(73) Assignee: Nobel Biocare AB (publ), Gothenburg (SE)

( * ) Notice: Subject to any disclaimer, the term of this patent is extended or adjusted under 35 U.S.C. 154(b) by 0 days.

(21) Appl. No.: 09/787,391

(22) PCT Filed: Sep. 1, 1999

(86) PCT No.: PCT/SE99/01499

§ 371 (c)(1),
(2), (4) Date: Mar. 19, 2001

(87) PCT Pub. No.: WO00/15138

PCT Pub. Date: Mar. 23, 2000

(30) Foreign Application Priority Data

Sep. 17, 1998 (SE) .................................... 9803153

(51) Int. Cl.⁷ .......................... A61C 8/00; A61C 19/04
(52) U.S. Cl. ........................... 433/174; 73/761; 433/72
(58) Field of Search ................................. 433/172, 173, 433/174, 175, 176, 72, 73; 73/761

(56) References Cited

U.S. PATENT DOCUMENTS

| | | | | |
|---|---|---|---|---|
| 4,359,906 A | * | 11/1982 | Cordey ........................ 73/761 |
| 4,686,859 A | * | 8/1987 | Wallace ........................ 411/14 |
| 5,343,759 A | * | 9/1994 | Hesthamar et al. ............ 73/761 |
| 5,571,971 A | * | 11/1996 | Chastel et al. ................. 73/761 |
| 5,591,919 A | * | 1/1997 | Hathaway et al. ........ 29/407.02 |
| 6,204,771 B1 | * | 3/2001 | Ceney ................... 250/559.19 |
| 6,358,051 B2 | * | 3/2002 | Lang et al. .................. 433/173 |

* cited by examiner

Primary Examiner—Cary E. O'Connor
(74) Attorney, Agent, or Firm—Connolly Bove Lodge & Hutz LLP

(57) ABSTRACT

An instrument is connected to a driving-in tool or drilling tool for elements on or in the form of an implant or drill for dentine. The tool includes an electric motor, the torque of which can be sensed, and which can be controlled by a control unit. A display unit is arranged so as to partly or fully display a curve representing the driving-in function performed. A tightening function is determined by a scale based on the slope of the curve, wherein a flatter slope represents a lower quality function and a steeper slope represents a higher quality function. A frictional resistance which exists for an element during the driving-in of the element can be determined in order to allow secure locking (preload) of the element by tension in the material of the element. A torque-time curve can be used assess the bone quality of bone being implanted or drilled.

Figure 1:
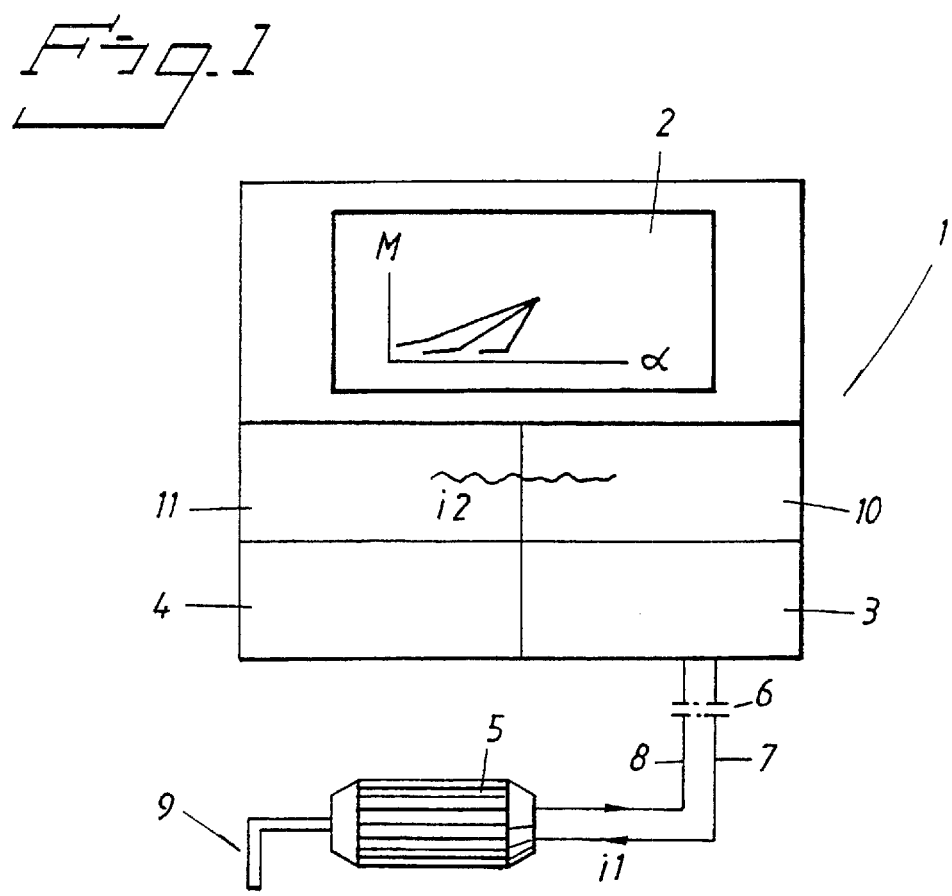

14 Claims, 3 Drawing Sheets

ARRANGEMENT FOR AN INSTRUMENT WHICH COMPRISES OR IS CONNECTED TO A DRIVING-IN TOOL

TECHNICAL FIELD

The present invention relates to an arrangement for an instrument or such an instrument which comprises or is connected to a screwing-in or tightening tool, referred to here as a driving-in tool, for elements on or in the form of an implant or drill for bone, in particular dentine. In this connection, the tool comprises an electric motor which can be controlled by a control unit. Also included is a unit which senses feed current in the electric motor and, depending on the sensing, emits a signal depending on the torque of the electric motor, by means of which signal a torque or torque-angle curve can be represented. Also included is a display unit which is arranged so as to display fully or partly a driving-in or tightening function performed. Thus the display unit can display, for example, curves or collected or individual values.

STATE OF THE ART

The present invention constitutes a development of inter alia the equipment indicated in PCT publication WO 98/27886, which relates to a surgical instrument to which a tightening tool according to the above can be connected and which instrument includes a display unit in order to display inter alia a torque-angle value. The instrument is used inter alia to screw implants or fixtures tight in the dentine. The instrument can also be used to screw down a screw tap in a hole made in the dentine. Furthermore, the instrument can be used to screw elements in the form of screws tight in association with said implants and spacer elements belonging to these and other prosthetic constructions. The known instrument comprises a control unit for controlling the electric motor and also sensing means which sense the current in the feed circuit of the motor and, depending on the sensing, supply information to microprocessor-based equipment.

The present invention is also based on what is previously known through PCT publication WO 95/20146 which indicates equipment for inter alia screw-driving and in which the structure in question must fit against the interacting structure with a high degree of accuracy. One of the main objects of this invention is that there are not to be any residual stresses or strains which are built into the structure as a result of assembly.

DESCRIPTION OF THE INVENTION

TECHNICAL PROBLEM

There is a requirement to be able to improve further the previously known instruments. In this respect, it is desirable in practice, for example, to be able to perform practical analysis aimed directly at the quality of the driving-home or tightening function in screw joints. The invention solves this problem inter alia.

It is also desirable to have a simple and readily understandable indication of the quality of the tightening function in question. The invention solves this problem also.

In connection with the driving-home of screws in implants or equivalent, the screwing-in function can be impaired by bone penetrating, for example, between fixture and spacer. Another source of defects may be that the spacer in question is not sufficiently well fitted or anchored on the implant. A further factor which can distort the driving-home function is if the entire prosthetic function as such is poorly aligned. There is a requirement for sources of defects of said type not to be capable of impairing the driving-home result, but for it to be possible to detect them at an early stage during the installation work. The invention solves this problem also.

There is a requirement to be able to determine and check a desired or predetermined anchoring load in the element or screw concerned or the securing force in the screw connection. The invention solves this problem also.

There is in this respect a requirement to be able to identify the frictional resistance the element or screw encounters in the screwing-in function concerned. The invention solves this problem also.

There is also a requirement to be able to evaluate or assess the bone quality during ongoing implant preparation. According to previously known instruments, the bone hardness can be evaluated during preparation in connection with threading of a prepared hole using a screw tap or a self-tapping fixture. The disadvantage of previously known methods is that the surgeon has an opportunity to establish the bone quality only after the hole has been drilled. It would be a great advantage if the surgeon could know the bone hardness before making a decision on which drill diameter to use for the final preparation. The invention aims to solve this problem inter alia.

There is also a requirement to be able to establish, during the driving-in function, whether the implant is rotating without following the pitch of the implant in the axial direction, which means that the threads are being destroyed in the bone. The invention aims to solve this problem also.

SOLUTION

An arrangement of the type referred to in the introduction can be considered to be characterized mainly in that the sensing and/or display unit determines the quality of the tightening function by means of a scale based on the slope of the torque-angle curve produced. According to the invention, a flatter slope of the curve represents lower quality and a steeper slope represents high quality.

The invention can also be considered to be characterized mainly in that a calculating unit, for example in the sensing and/or display unit, is arranged so as to determine, in the tightening function, a frictional resistance which exists for the element during its driving-in or screwing-home in order to make possible the application of an accurate desired or predetermined loading which brings about secure locking (preload) of the element by means of tension or elasticity movement in the material of the element.

In a development of the inventive idea, the element consists of a screw associated with the implant/the fixture and the spacer. The display unit can in this connection be arranged so as to display said scale, for example a scale running between 1 and 10, where 10 indicates good quality and 1 indicates poor or inferior quality. The slope can be defined with a starting point from a base value of the torque. The slope can also be defined from a base value up to the maximum torque value in question and also by means of the range of degrees of rotation for the sloping part concerned of the curve.

Said developments can also relate to a screw which is first intended to be screwable home with frictional resistance inter alia via its screw thread and can then be anchored by means of tension or elasticity in the screw material (preload) which is required for the anchoring loading on the screw.

Said calculating unit can operate with a torque value which constitutes part of a set torque value and brings about tightening of the element or screw. In this connection, a first measured value can be established. The calculating unit can also establish a second measured value when the element or screw is subsequently loosened. Taking as its starting point said first and second value, the calculating unit can work out a frictional resistance according to a formula indicated below. The calculating unit can then work out the torque value in question by means of adding to the frictional resistance worked out a value which gives the desired or predetermined secure-locking loading (preload) on the element.

An arrangement for evaluating the bone quality during implant preparation can be considered to be characterized mainly in that the sensing unit senses torque generated by the electric motor during drilling in the bone, in particular dentine, of a hole for a screw tap or a threaded implant, and in that the display unit indicates, depending on the sensing, a torque-time curve, by means of which the quality of the bone can be read off during drilling.

In developments of the inventive idea, the sensing unit senses the torque during drilling and the calculating unit is then arranged so as to calculate power consumption per millimeter of drilled hole/implant. Empirical evaluations can also be included as a component in the quality read-out. A curve displayed on the display unit indicates the average power per millimeter of implant. The drill speed can also be included in the calculation.

The invention is further characterized in that the sensing unit senses torque generated by the electric motor during tapping of the implant into the bone, preferably the dentine, and in that a calculating unit, for example in the sensing or display unit, is arranged so as to establish, during the driving-in function, whether the implant is rotating without following the pitch of the implant in the axial direction, that is to say the threads are being destroyed in the bone, and also in that said arrangement warns the user that this is taking place or stops the rotation of the implant.

ADVANTAGES

By means of the proposals made above, previously known instruments can be supplemented with new functions which are of value in being able to perform the practical work. The possibility of integration into known instruments has economic advantages. Furthermore, it is possible to prevent stresses being built into the implant constructions with implants, spacers etc. The torque-speed curve in question during drilling can give the user sufficient information for interpreting his/her own actions because he/she knows his/her own drilling style and the arrangement can therefore be an extremely valuable diagnostic tool. As the user also establishes more and more references in the actions he/she takes, the accuracy of interpretation will increase.

LIST OF FIGURES

Figure 2:
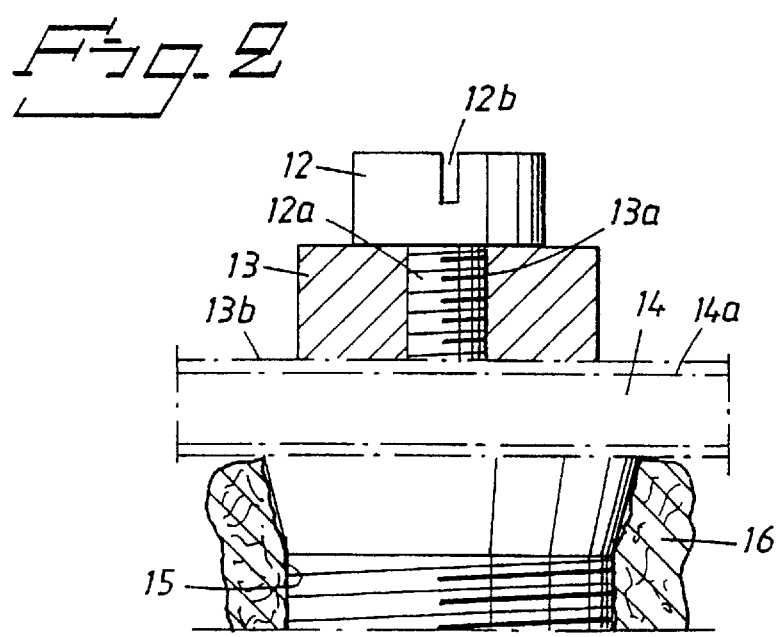
Figure 3:
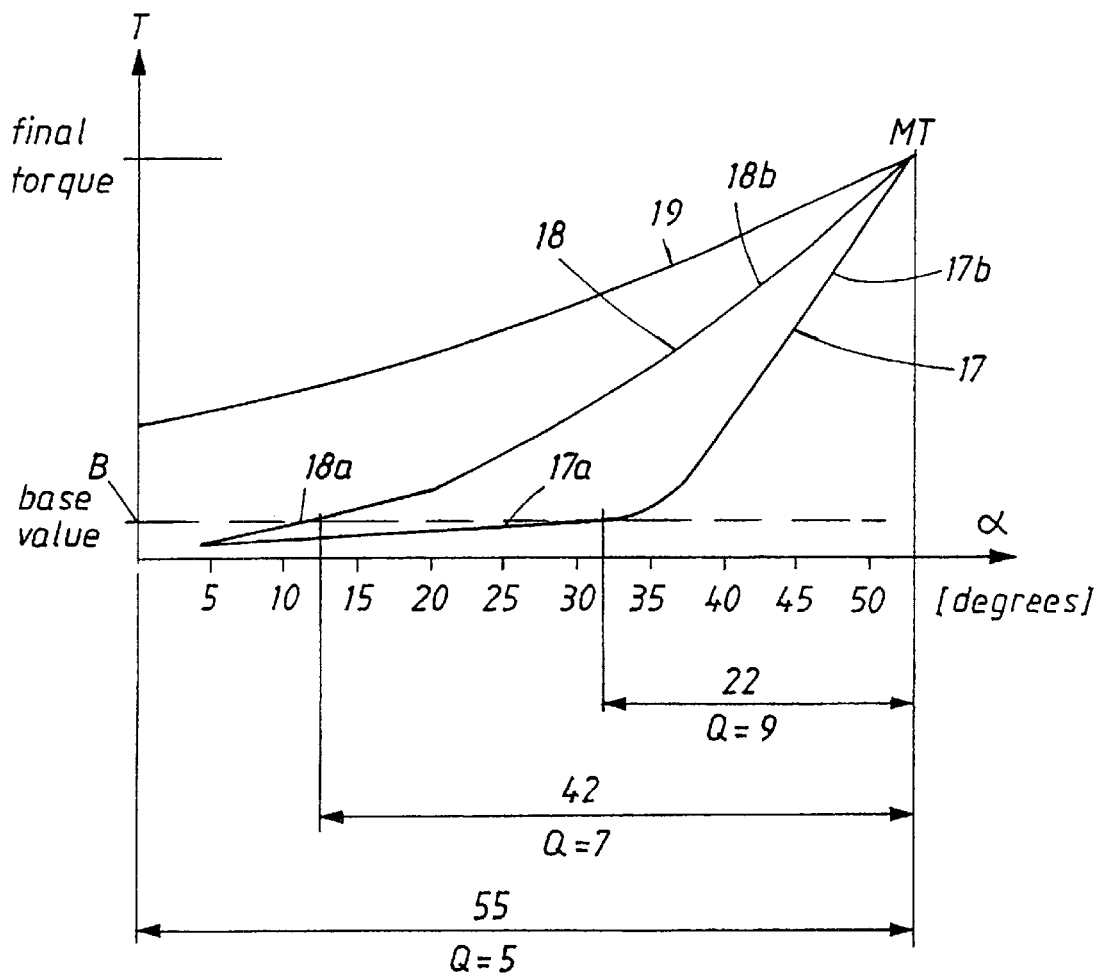
Figure 4:
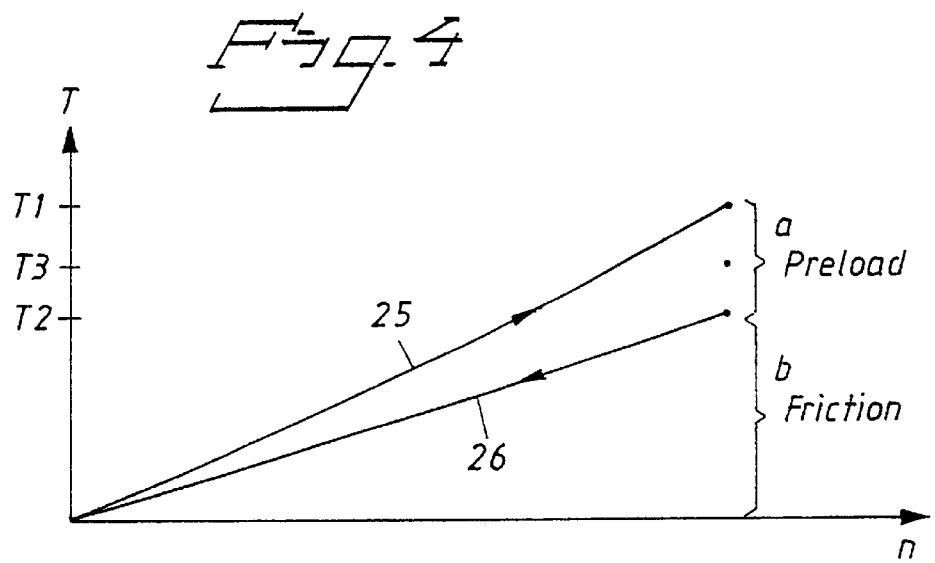
Figure 5:
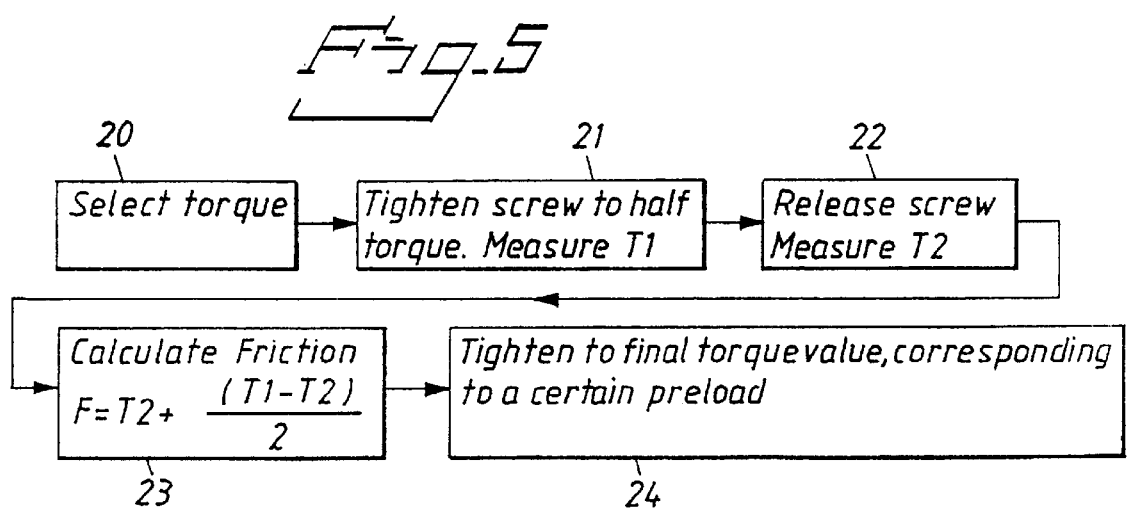
Figure 6:
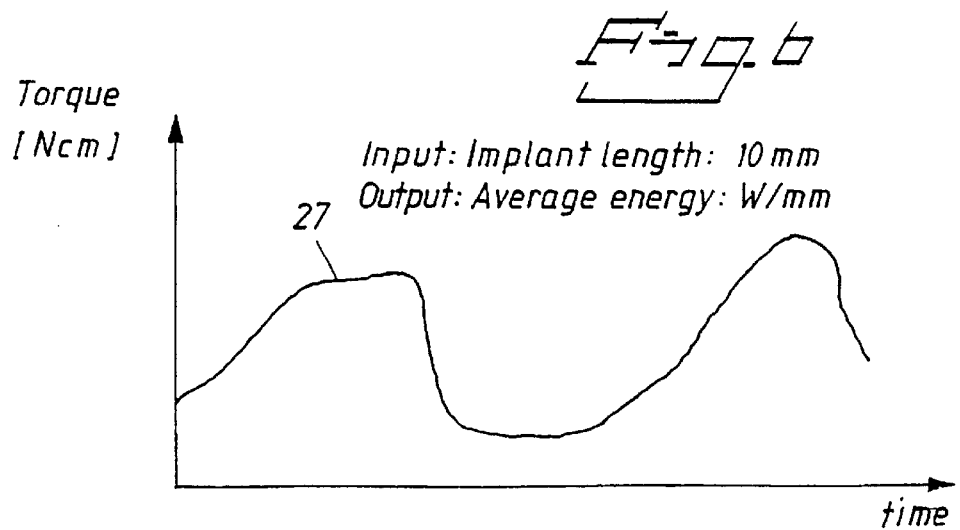

A for the present proposed embodiment of an arrangement which has the significant characteristics of the invention is described below with simultaneous reference to the appended drawings, in which FIG. 1 shows in the form of a basic diagram and from the front, a surgical instrument and, connected thereto, an electric motor with a tool for acting on an element, FIG. 2 shows in partial vertical section an example of a screw in a partly shown implant and spacer element, FIG. 3 shows a torque-angle graph, FIG. 3a shows a table defining quality values of tightening values, FIG. 4 shows a torque graph, FIG. 5 shows a functional diagram which can be implemented in a calculating unit or equipment used, and FIG. 6 shows in screw form a torque-time curve for evaluating or assessing bone quality during implant preparation.

DETAILED EMBODIMENT

In FIG. 1, a surgical instrument is indicated by 1. The instrument comprises a display unit 2 which can consist of a data screen, a VDU, lamp arrangement etc. In the case of a screen, the instrument can represent torque-angle curves, all or parts of a screw-tightening result, the quality-determination function etc. The instrument comprises in a manner known per se a power supply unit 3 and a unit 4 which controls an electric motor 5 connected to the instrument. The connection is in this respect made via a symbolically indicated connection 6, and two of the connecting conductors of the motor are indicated, namely 7 and 8. The electric motor or the tool part 5 has in a manner known per se a unit 9 performing screw-tightening. The instrument also comprises a unit 10 which senses the feed current i1 of the electric motor, and also a calculating unit 11. The instrument is itself microcomputer-based and also comprises memory functions in accordance with known corresponding instruments. By means of the unit 10 and/or 11, a signal i2 depending on the sensing is obtained.

FIG. 2 relates to a screw function on the implant, shown quite generally. A screw is indicated by 12 and parts of a spacer element or another construction element are shown by 13. The element is arranged on an implant 14 which is partly shown. The implant is intended to be screwable home in a premade hole 15 in dentine 16. The screw 12 is provided with a thread 12a which can be screwed into an internal thread 13a in the element 13.

The tool 5 to 9 can thus be applied to a screw slot 12b on the screw. According to the idea of the invention, a practical analysis is to be performed by the instrument with direct feedback on the quality in the tightening function in the screw connection 12, 13 via the threads 12a and 13a respectively. As the screw 12a is tightened, a corresponding torque-rotation curve according to FIG. 3 is obtained. FIG. 3 shows three different curves 17, 18 and 19. The vertical axis of the graph shows the torque values, while the horizontal axis shows the degree value α. A base value B for the torque is indicated in the graph by a dashed line parallel to the horizontal axis. Also indicated is a point MT which indicates the maximum torque value in the case concerned. The curve 17 has a flat part 17a which follows the base value B and also a sloping part 17b which slopes relatively steeply. Correspondingly, the curve 18 has a part 18a which essentially follows the base value B and merges with a sloping part 18b which has a gentler slope than the slope 17b of the curve 17. The curve 19 does not have a part following the base value B but has a shape which essentially slopes throughout up to the value MT at the outer degree value. The slope of the curve 19 is flatter than the slopes 17b and 18b of the curves 17 and 18. The slope 17b extends between degree values 30–55 roughly and a more accurately worked out degree value range is indicated by 22 in the diagram. The slope 18b extends from degree value 12 to 55 roughly and the degree value range is in this case indicated by 42. The curve slope of the curve 19 extends over the majority of the degree value range indicated, which, for the curve 19, has been indicated as 55.

By means of the arrangement, a quality index can be obtained. The index or the scale can extend between 1 and 10, where 10 means good quality and 1 means poor quality. The quality of the tightening can be impaired by bone being present between the spacer and the implant (cf. the surfaces 13b and 14a in FIG. 2). Other aggravating circumstances may be that the spacer 13 is not satisfactorily fitted to the implant 14 or that the entire installation arrangement of implant, spacer etc. is poorly aligned. If one, two or all three of the above problems are present, the curves will be relatively flat, compare the curve parts 17b and 18b and also the curve 19. According to the above, the index or the quality is calculated from a degree value range from said base value B up to the maximum torque MT.

The table according to FIG. 3 indicates the quality divided into a 10° scale. The maximum quality 10 exists if the curve slope begins at 45° and reaches the maximum value MT from the base value. The degree value range is in this case 10°, that is to say the Q value=10. The next stage is if the curve slope extends from roughly 35° to 55° and reaches the maximum value MT within this degree value range etc. On this calculation basis, the curve 17 has a value of Q=9, the curve 18 a value of Q=7, and the curve 19 a value of Q=5.

According to FIGS. 4 and 5, a method and arrangement for determining and controlling the anchoring force (preload) in a screw connection are made possible. The torque required in order to tighten a screw connection can in principle be divided into two parts, namely on the one hand friction and on the other hand the torque required to tension or bring about elasticity movement in the screw to a given anchoring load (preload). The problem with using existing torque-controlling methods for determining the anchoring load is that if the friction differs between different screw connections and the connection is to be controlled by checking the torque applied, the anchoring loading (preload) will differ. If the screw 12 is tightened, the torque for this can be shown on the display unit 2. The torque will rise from close to 0 to a certain value, compare FIG. 4. The torque will then be equal to friction+anchoring load. If the screw is loosened, the torque shown will be equal to friction−anchoring load. If the screw is first tightened and subsequently loosened again, it is possible to calculate or work out the anchoring value in question and thus the friction also. The screw can then be tightened to its final torque value, which is worked out in such a manner that the friction component is eliminated and that a very accurate anchoring load can then be applied in the screw connection, compare the screw 12 and the element 13 in FIG. 2. According to the new arrangement and method, the functional diagram according to FIG. 5 is followed. In a first stage 20, a torque is selected. The screw is then tightened to half torque, and a measured value T1 is read off according to 21. The screw is then loosened, after which a measured value T2 is recorded according to box 22. Using the values thus measured, the calculating unit (cf. 11 in FIG. 1) can work out a friction according to the formula F=T2+(T1−T2)/2, cf. block 23 in FIG. 5. Tightening to the final torque value, which corresponds to a certain or predetermined value for anchoring or tensioning, can then be carried out, compare block 24. The above is also indicated in FIG. 4 where the vertical axis shows the torque T and the horizontal axis shows the rotary movement n. The values T1 and T2 are indicated on the vertical axis. A value T3 is also shown, as are a range a which indicates the anchoring loading and a range b which indicates the friction. Two curves are shown by 25 and 26.

According to the present invention, a possibility is afforded for improved assessment or evaluation of the bone quality during ongoing implant preparation or drilling of holes in dentine. It is possible per se to measure the torque during drilling and also the speed of the drill. These parameters will make it possible to represent the input power and, with knowledge of time and implant length, it is possible to calculate in said calculating unit 11 (see FIG. 1) the average input power per millimeter of implant. In order to obtain an accurate picture of the bone quality, the drilling depth would need to be included so as to obtain the power per millimeter of implant continuously for the entire implant length. However, the torque-implant rotation curve 27 during drilling provides the user with sufficient information to interpret his or her own actions because he/she knows his or her own drilling style and the result can therefore be a useful diagnostic tool.

In FIG. 6, the vertical axis shows the torque in Ncm and the horizontal axis shows time. An input value can in this connection be that the implant length is 10 mm. The output value gives the average power W/mm.

It is also possible to see on the graph whether the implant, during tapping, is rotating without going in. This would mean that the threads are being destroyed in the bone. The arrangement can therefore be provided with means which indicate such a case. The sensing unit senses torque generated by the electric motor during tapping of the implant into the bone, and a calculating unit, for example in the sensing or display unit, is arranged so as to establish, in the driving-in function, whether the implant is rotating without following the pitch of the implant in the axial direction. If this is the case, a warning signal is given to the user or the rotation of the implant is stopped.

The invention is not limited to the embodiment shown above by way of example but can undergo modifications within the scope of the patent claims below and the inventive idea.

What is claimed is:

1. Arrangement for an instrument which comprises or is connected to a driving-in tool for an element on or in the form of an implant or drill for bone, in which the tool comprises an electric motor which can be controlled by a control unit, and in which a unit which senses feed current in the electric motor and, depending on sensing of the feed current, emits a signal depending on the torque of the electric motor, which signal represents a torque curve or torque-angle curve, and in which a display unit is arranged so as to display fully or partly a driving-in function performed, according to one or more of the following alternatives:

a) at least one of the sensing and display unit determines a quality of the tightening function by means of a scale based on a slope of said torque curve or said torque-angle curve, wherein a flatter slope represents lower quality of the tightening function and a steeper slope represents higher quality of the tightening function;

b) a calculating unit in one of the sensing unit and the display unit is arranged so as to determine, in the driving-in function, a frictional resistance which exists for the element, when the element is in the form of a screw, during driving-in of the element in order to make possible the application of a desired loading which brings about secure locking by means of tension or elasticity movements in material of the element;

c) the sensing unit senses torque generated by the electric motor during drilling in the bone of a hole for a screw tap or a threaded implant, and that the display unit indicates, depending on the sensing of the feed current, a torque-time curve, wherein a quality of the bone can be read off during drilling based on the torque-time curve;

d) the sensing unit senses torque generated by the electric motor during tapping of the implant into the bone, and that a calculating unit in one of the sensing and the display unit, is arranged so as to establish, in the driving-in function, whether the implant is rotating without following a pitch of the implant in an axial direction and threads are thereby being destroyed in the bone, in which case a warning signal is given to a user or rotation of the implant is stopped.

2. Arrangement according to claim 1, wherein the element consists of a screw associated with the implant and spacer, and wherein at least one of bone being present between the implant and the spacer, the spacer having a poor connection to the implant and the spacer and the implant having poor alignment contributes to imparting to the torque curve or the torque-angle curve a flatter slope compared with a case in which connection and alignment of the implant and spacer are correct.

3. Arrangement according to claim 1, wherein the display unit displays a scale running between 1 and 10, where 10 indicates good quality and 1 indicates poor quality.

4. Arrangement according to claim 1, wherein the slope is defined with a starting point from a base value of the torque.

5. Arrangement according to claim 1, wherein the slope is defined from the base value up to the maximum torque value in question and also by the range of degrees of rotation for the sloping part concerned of the curve.

6. Arrangement according to claim 1, wherein the element consists of a screw which can first be screwed home with frictional resistance inter alia via its screw thread and can then be anchored by means of tension or elasticity movement in the screw material which is required for anchoring loading of the screw.

7. Arrangement according to claim 1, wherein the calculating unit operates with a torque value which constitutes part of a set torque value and brings about tightening of the element or screw, and wherein, in this connection, a first measured value can be established.

8. Arrangement according to claim 1, wherein the calculating unit establishes a second measured value when the element or screw is loosened.

9. Arrangement according to claim 1, wherein the calculating unit works out the frictional resistance according to $F=T2+(T1-T2)/2$.

10. Arrangement according to claim 1, wherein the calculating unit works out the torque value in question by means of adding to the frictional resistance worked out or the force for this force which gives the desired or predetermined tightening loading (preload) on the element or screw.

11. Arrangement according to claim 1, wherein the sensing unit senses the torque during drilling, and wherein the calculating unit is arranged so as to determine power consumption per millimeter of implant.

12. Arrangement according to claim 1, wherein empirical evaluations are included in a read-out function for bone quality.

13. Arrangement according to claim 1, wherein a curve displayed by means of the display unit indicates average power per millimeter of implant.

14. Arrangement according to claim 1, wherein drill speed is also included in calculations related to the driving-in function.

* * * * *